US008614707B2

(12) United States Patent
Warsito et al.

(10) Patent No.: US 8,614,707 B2
(45) Date of Patent: Dec. 24, 2013

(54) 3D AND REAL TIME ELECTRICAL CAPACITANCE VOLUME-TOMOGRAPHY SENSOR DESIGN AND IMAGE RECONSTRUCTION

(75) Inventors: Warsito Warsito, Tangerang (ID); Qussai Marashdeh, Columbus, OH (US); Liang-Shih Fan, Columbus, OH (US)

(73) Assignee: The Ohio State University, Columbus, OH (US)

( * ) Notice: Subject to any disclaimer, the term of this patent is extended or adjusted under 35 U.S.C. 154(b) by 1437 days.

(21) Appl. No.: 11/909,548

(22) PCT Filed: Mar. 22, 2006

(86) PCT No.: PCT/US2006/010352
§ 371 (c)(1),
(2), (4) Date: Mar. 14, 2008

(87) PCT Pub. No.: WO2006/102388
PCT Pub. Date: Sep. 28, 2006

(65) Prior Publication Data
US 2010/0097374 A1   Apr. 22, 2010

Related U.S. Application Data

(60) Provisional application No. 60/760,529, filed on Jan. 20, 2006, provisional application No. 60/664,026, filed on Mar. 22, 2005.

(51) Int. Cl.
*G06T 17/00* (2006.01)
(52) U.S. Cl.
USPC ................ 345/420; 345/419; 345/424; 378/4
(58) Field of Classification Search
None
See application file for complete search history.

(56) References Cited

U.S. PATENT DOCUMENTS

| 5,365,560 | A * | 11/1994 | Tam ................................. 378/8 |
| 7,496,450 | B2 * | 2/2009 | Ortiz Aleman et al. ........... 702/6 |
| 8,116,430 | B1 * | 2/2012 | Shapiro et al. .................. 378/65 |
| 2003/0031291 | A1 * | 2/2003 | Yamamoto et al. ............. 378/41 |
| 2004/0028181 | A1 * | 2/2004 | Charles, Jr. et al. ............. 378/92 |
| 2004/0233191 | A1 * | 11/2004 | Mukherjee et al. ........... 345/419 |

OTHER PUBLICATIONS

Marashdeh, et al., "On the ECT Sensor Based Dual Imaging Modality System for Electrical Permittivity and Conductivity Measurements", 2006, pp. 1-6, Ohio State University, Columbus, Ohio
Warsito, et al., "Electrical Capacitance Volume Tomography", 2007, pp. 1-9.

* cited by examiner

*Primary Examiner* — Said Broome
(74) *Attorney, Agent, or Firm* — Standley Law Group LLP

(57) ABSTRACT

Dynamic three-dimensional image electrical capacitance tomography sensor system is disclosed. The technique generates, from the measured capacitance, a whole volume image of the region enclosed by the a geometrically three-dimensional capacitance sensor. A real time, three-dimensional imaging of a moving object or a real time volume imaging (i.e., four-dimensional (4D)) allows for a total interrogation scheme of the whole volume within the domain of an arbitrary shape of geometry to be implemented. The system comprises a 3D capacitance sensor, data acquisition electronics and the image reconstruction algorithm which enables the volume-image reconstruction. The electrode shape of the capacitance sensor can be rectangular, triangular, trapezium, or any shape to enclose a 3D section of the measuring domain and to distribute the electrical field intensity in three directions with equal sensitivity strength. The image reconstruction algorithm reconstructs simultaneously the image voxels in a three-dimensional array. The tomography sensor system may be multimodal.

37 Claims, 15 Drawing Sheets

3D AND REAL TIME ELECTRICAL CAPACITANCE VOLUME-TOMOGRAPHY SENSOR DESIGN AND IMAGE RECONSTRUCTION

The present invention generally relates to process tomography and, in particular, relates a dynamic three-dimensional image electrical capacitance tomography.

The recent progress in the development of such measuring techniques as process tomography has provided more insights into complex multiphase flow phenomena in many industrial processes often in a combination gas, liquid and solid states, including pneumatic conveying, oil pipe lines, fluidized beds, bubble columns and many other chemical and biochemical processes. The technique is capable of monitoring and control, both continuously and simultaneously, the local and global dynamic behavior of gas bubbles and solid particles in a non-invasive manner. Among available tomography techniques, electrical tomography, including capacitive, conductive or inductive modalities, is the most promising technical for dynamic flow imaging purpose. The technique has a relative high temporal resolution, up to a few milliseconds, with sufficient spatial resolution, up to 1 to 3% of column diameter. The high speed capability of electrical tomography systems is demonstrated in the recent development for up to 1000 frames per second capture rate. Earlier work on the development of real time ECT has demonstrated the accuracy of an image reconstruction technique based on the Hopfleld neural network optimization (i.e., neural network, multi-criteria image reconstruction technique (NN-MOIRT)).

Tomography technique, in general, generates a two-dimensional image called a "tomogram" (i.e., a two-dimensional (2D) image). A three-dimensional image of an object is usually generated by stacking up the tomograms. This is termed "static" three-dimensional (3D) imaging, because the 3D image could only be generated from a static or slow moving object. Therefore, this 3D imaging cannot be applied to situations with a fast moving object, or highly fluctuating multiphase flow media. For conventional ECT, 2D ECT in particular, the tomogram is reconstructed from a capacitance sensor, which is in fact, geometrically three-dimensional. Unlike an electromagnetic transmission tomography, slice imaging is not possible for ECT due to the extended length of the electrode. The obtained 2D image is a result from projections of the object on a cross-section by assuming no variation in the axial direction. Therefore, the 2D ECT is actually unreal in the sense that the three-dimensional object needs to be assumed to have an infinite length. This is one of the major drawbacks of conventional ECT, and becomes problematic when the variation in the permittivity along the axial direction is significant. Fortunately, electrical tomography, either resistance or capacitance, has a potential for volumetric imaging, as electrical current or wave, spreads to the three-dimensional space. The "soft-field" effect of the electrical field is once considered as one disadvantage of the technique for imaging applications, but it may be advantageous to realize the volumetric imaging based on tomography technique.

Additionally, electrical tomography is typically implemented based on measurements of a single constitutive property (i.e., permittivity for capacitance tomography, conductivity for resistive and impedance tomography and permability for induction tomography). However, the need for real-time imaging of complex processes involving multiphase components have motivated in recent years the development of imaging systems based on multiple electrical properties, i.e., multimodal tomography.

Multimodal tomography is generally implemented through three different strategies: (1) integration of two or more tomography hardware sensors into one imaging system (e.g., gamma-ray and ECT tomography), (2) use of reconstruction techniques capable of differentiating between different phases based on the same sensing signal (e.g., NN-MOIRT), and (3) use of the same sensor hardware to acquire different signals corresponding to different electrical properties (impendence tomography sensors for imaging permittivity and conductivity). Although the first strategy is fast, it has the major disadvantage in terms of its high cost and complexity (added hardware). In addition, the data acquisition needs to be carefully coordinated to yield consistent data at different given time frames for real-time applications. The second strategy is the least costly to implement. However, it yields relatively longer reconstruction time due to more involved reconstruction algorithms. The third strategy is inherently multi-modal since it provides all the required information (on the different electrical properties) using the same sensor hardware and same reconstruction technique. Moreover, integration of such systems with multi-modal reconstruction techniques can provide independent data for different phases in the imaging domain. For example, obtaining both capacitive and conductive (impedance) flow information simultaneously is beneficial in many applications. This is particularly true when the flow under consideration is a mixture of phases with widely different conductivity and permittivity constants, such as oil flow in a pipeline.

Electrical impedance tomography (EIT) has been extensively used for both medical and industrial applications. Although EIT commonly refers to unimodal resistivity tomography systems, it can also be used for permittivity/conductivity imaging by considering amplitude and phase measurements of the interrogating signal. However such applications depend on current injection measurement technologies used to acquire the electrical signal, which requires direct contact between the sensor and imaging domain. This is not viable when an insulating elements separates the flow of interest from the sensor system, as is the case in many industrial processes. For those applications, one common requirement for the tomographic system is to be both non-invasive (i.e., not in direct contact with the domain of interest) and non-intrusive (i e., not to affect the process under examination).

Therefore, there is a need for an ECT application for "dynamic" three-dimensional image reconstruction technique, namely electrical capacitance volume-tomography (ECVT). This technique generates, from the measured capacitance, a whole volume image of the region enclosed by a geometrically three-dimensional capacitance sensor. The principle components of this technique includes a three-dimensional capacitance sensor, data acquisition electronics and an image reconstruction algorithm which enables the volume-image reconstruction.

There is also a need for a new non-invasive multimodal tomography system based on the use of ECT sensor technology. Unlike usual ECT sensor operation that assumes a static interrogating field, the interrogating field of the system operates under quasi-static conditions. The sensor is used to simultaneously measure variations in both capacitance and power corresponding to permittivity and conductivity distribution, respectively, within the sensing domain, or vessel. A dual capacitance/power sensivity matrix is obtained and used in the image reconstruction algorithm.

According to the present invention, dynamic three-dimensional image electrical capacitance tomography sensor system is disclosed. The technique generates, from the measured capacitance, a whole volume image of the region enclosed by the a geometrically three-dimensional capacitance sensor. A real time, three-dimensional imaging of a moving object or a real time volume imaging (i.e., four-dimensional (4D)) allows for a total interrogation scheme of the whole volume within the domain of an arbitrary shape of geometry to be implemented. The system comprises a three-dimensional capacitance sensor, data acquisition electronics and the image reconstruction algorithm which enables the volume-image reconstruction. The electrode shape of the capacitance sensor can be rectangular, triangular, trapezium, or any shape that encloses a three-dimensional section of the measuring domain and that distributes the electrical field intensity in three directions with equal sensitivity strength or comparable sensitivity strength. The image reconstruction algorithm reconstructs simultaneously the image voxels in a three-dimensional array. The tomography sensor system may also be multimodal.

In accordance with embodiment of the present invention, ECVT is also applicable for 3D medical imaging of the human body.

In accordance with another embodiment of the present invention, ECVT is also feasible for real time imaging of multiphase flow systems.

In accordance with yet another embodiment of the present invention, ECVT is also feasible interrogation of the whole vessel or conduit with an arbitrary shape of geometry.

Accordingly, it is a feature of the embodiments of the present invention to produce real time three-dimensional imaging of a moving object, or real time four-dimensional volume imaging.

It is another feature of the embodiments of the present invention to produce real time three-dimensional imaging of a moving object, or real time four-dimensional volume imaging using different shape measuring electrodes as long as the sensor provides three-dimensional sensitivity distribution with relatively equal sensitivity strength or with comparable sensitivity strength.

It is a yet another feature of the embodiments of the present invention to produce real time three-dimensional imaging of a moving object, or real time four-dimensional volume imaging, using greater than two planes of electrodes to provide better variation in the axial direction.

It is a still another feature of the embodiments of the present invention to apply the volume imaging of multiphase systems in conduits such as pipe bends, T-junctions, conical vessels or other complex geometric systems.

It is a still yet another feature of the embodiments of the present invention to apply the volume imaging technique for real time three-dimensional medical imaging of the human body and for the monitoring of tablet manufacturing in the pharmaceutical industry.

Other features of the embodiments of the present invention will be apparent in light of the description of the invention embodied herein.

The following detailed description of specific embodiments of the present invention can be best understood when read in conjunction with the following drawings, where like structure is indicated with like reference numerals and in which:

FIGS. 1A-B illustrate possible sensor designs according to one embodiment of the present invention.

Figure 1A:
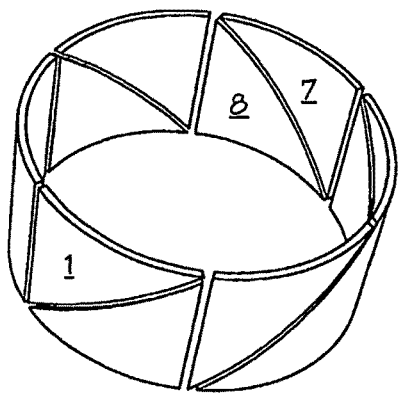
FIG. 1C illustrates volume image digitization according to one embodiment of the present invention.

In the following detailed description of the embodiments, reference is made to the accompanying drawings that form a part hereof, and in which are shown by way of illustration, and not by way of limitation, specific embodiments in which the invention may be practiced. It is to be understood that other embodiments may be utilized and that logical, mechanical and electrical changes may be made without departing from the spirit and scope of the present invention.

A technique to reconstruct simultaneously a volume image of a region inside a vessel from capacitance measurement data using capacitive sensor electrodes attached on the wall of the vessel is developed. Due to the "soft field" nature of the electrical field, the capacitance measurements can be made using arbitrary shapes of electrodes and vessels. The term "volume tomography" instead of 3D tomography stems from the fact that the technique generates simultaneous information of the volumetric properties within the sensing region of the vessel with an arbitrary shape. The terminology is also chosen to differentiate the technique from a "static" 3D or quasi-3D tomography technique. The development of the technique primarily includes the evaluation of the capacitance tomography sensor design and volume image reconstruction algorithm. The tests on capacitance data set obtained from actual measurements are also shown to demonstrate the validity of the technique for real time, volume imaging of a moving object.

Principle of ECT

An ECT sensor generally consists of n electrodes placed around the region of interest, providing n(n−1)/2 independent mutual capacitance measurements used for image reconstruction. Unlike usual EIT sensors that use direct current injection as excitation signal, ECT sensors rely on a time varying driving signal for capacitance measurements.

Applying a quasi-static approximation in Maxwell's equations, the electric field distribution obeys the following equation:

$$\nabla \cdot (\sigma + j\omega \in) \nabla \phi = 0, \quad (1)$$

where $\phi$ is the electric potential, $E = -\nabla \phi$ and E is the electric field intensity, $\omega$ is the angular frequency, $\sigma$ is the conductivity, and $\in$ is the permittivity. The mutual capacitance between any two pair of electrodes i and j, source and detector, is obtained through:

$$C_{ij} = \frac{1}{\Delta V_{ij}} \oint_{\Gamma_j} \varepsilon \nabla \phi \cdot \hat{n} dl \quad (2)$$

where $C_{ij}$ represents the mutual capacitance between electrodes i and j, $\Delta V_{ij}$ the potential difference, $\Gamma_j$ is a closed surface (or path in 2-D as considered here) enclosing the detecting electrode, and n̂ is the unit vector normal to $\Gamma_j$. Moreover, the r.m.s. power dissipated by a conductive object in the domain of interest is given by:

$$P = \frac{1}{2} \int_\Omega \int \sigma |\nabla \phi|^2 dS, \quad (3)$$

Equations (2) and (3) relate the permittivity and conductivity distributions to the boundary measurements of capacitance and power, respectively. The solutions of both equations given a $\sigma(x, y)$ and $\in(x, y)$ distribution constitutes the forward problem solution. The process of obtaining $\sigma(x, y)$ and $\xi(x, y)$ distributions from the boundary measurements is the inverse problem.

The Forward Problem:

Again, the electrical capacitance tomography (ECT) involves tasks of collecting capacitance data from electrodes placed around the wall outside the vessel (forward problem) and reconstructing image based on the measured capacitance data (inverse problem). The capacitance is measured based on the Poisson equation which can be written in three-dimensional space as:

$$\nabla \cdot \in(x,y,z) \nabla \phi(x,y,z) = -\rho(x,y,z) \quad (4)$$

where $\in(x,y,z)$ is the permittivity distribution; $\phi(x,y,z)$ is the electrical field distribution; $\rho(x,y,z)$ is the charge density. The measured capacitance $C_i$ of the i-th pair between the source and the detector electrodes is obtained by integrating Equation 4:

$$C_i = -\frac{1}{\Delta V_{ij}} \oint_{A_i} \int \varepsilon(x, y, z) \nabla \phi(x, y, z) dA \quad (5)$$

where $\Delta V_i$ is the voltage difference between the electrode pair; $A_i$ is the surface area enclosing the detector electrode. Equation 5 relates dielectric constant (permittivity) distribution, $\in(x,y,z)$, to the measured capacitance $C_i$.

The forward problem is dealt with generally in three approaches: linearization techniques; brute-force numerical methods such as finite element method and; (pseudo) analytical methods. Despite the fact that analytical methods provide accurate and relatively fast solutions, they are limited to very simple geometries with symmetric permittivity distributions, and are not applicable to industrial tomography systems with complex dynamic structures. On the other hand, numerical methods can provide fairly accurate solutions for arbitrary property distributions. They, however, consume excessive computational time which is impractical for tomography application with iterative image reconstruction. In this regard, linearization methods provide relatively fast and simple solution, though they show a smoothing effect on a sharp boundary of the reconstructed image. The smoothing effect is improved with iteration in the image reconstruction process.

The linearization technique using the so-called sensitivity model is based on the electrical network superposition theorem in which the domain (the cross section of the sensor) is subdivided into a number of pixels, and the response of the sensor becomes a sum (linear model) of interactions when the permittivity of one pixel only in the domain is changed by a known amount. This is similar to the first order series expansion approach for "hard field" tomography. Based on the sensitivity model, Equation 6 can be written as:

$$C_i = -\sum_j \varepsilon_j \frac{1}{\Delta V_{ij}} \oint_{A_i} \int \varepsilon(x, y, z) \nabla \phi(x, y, z) dA \quad (6)$$

The integration part divided by the voltage difference is called as sensitivity, which can be derived as:

$$S_{ij}(x_k, y_k, z_k) = \int_{V_0} \frac{E_i(x, y, z) \cdot E_j(x, y, z)}{V_i V_j} dx\,dy\,dz \quad (7)$$

where $E_i = -\nabla \phi$ is the electrical field distribution vector when i-th electrode is activated with $V_i$ while the rest of the electrodes are grounded, and $E_j$ is the electrical field distribution when j-th electrode is activated with voltage $V_j$ and the rest of the electrodes are grounded. $V_0$ is the volume of k-th voxel. Equation 5 can then written in matrix expression as:

$$C = SG \quad (8)$$

where C is the M-dimension capacitance data vector; G is N-dimension image vector; N is the number of voxels in the three-dimensional image; and M is the number of electrode-pair combinations. Specifically, N is equal to $n \times n \times n_L$, where n is the number of voxel in one side of image frame (layer); $n_L$ is the number of layers. The sensitivity matrix S has a dimension of M×N.

The Inverse Problem

The image reconstruction process is an inverse problem involving the estimation of the permittivity distribution from the measured capacitance data. In Equation 9, if the inverse of S exists, the image can be easily calculated.

$$G = S^T C \quad (9)$$

However, in most cases, especially electrical tomography, the problem is ill-posed, i.e., there are fewer independent measurements than unknown pixel values, so that the inverse matrix of S does not exist. The simplest way to estimate the image vector is using a back projection technique, i.e., in Equation 9, all measurement data are simply back-projected (added up) to estimate the image. This technique is referred to as linear back projection (LBP). Though the reconstructed image is heavily blurred due to a smoothing effect, the technique provides a rough estimation of the original shape of the image.

To obtain a shaper reconstructed image, usually an iterative method is employed. The iterative image reconstruction process involves finding methods for estimating the image vector G from the measurement vector C and to minimize the error between the estimated and the measured capacitance, under certain conditions (critera), such that:

$$SG \leq C \quad (10)$$

Mostly widely used iterative method to solve the problem in 2D ECT is Landweber technique, also called iterative linear back projection (ILBP), which is a variance of a steepest gradient descent technique commonly used in optimization theory. The technique aims at finding image vector G which minimizes the following least square error function, Equation 11.

$$f(G) = \frac{1}{2}\|SG - C\|^2 = \frac{1}{2}(SG - C)^T(SG - C) \quad (11)$$

The iteration procedure based on the steepest gradient descent technique becomes Equation 12.

$$G^{k+1} = G^k - \alpha^k \nabla f(G^k) = G^k - \alpha^k S^T(SG^k - C) \quad (12)$$

where $\alpha^k$ is a penalty factor of iteration k-th, which is usually chosen to be constant. The problem with the Landweber technique is that the reconstructed image is dependent on the number of iterations, and convergence is not always guaranteed. As seen in Equation 12, the image vector is corrected iteratively by the capacitance difference $\Delta C = (SG^k - C)$ multiplied by the sensitivity $S^T$ and the penalty factor. When the amount of capacitance data is limited, the capacitance difference $\Delta C$ becomes insignificant, and the image is iteratively corrected by the sensitivity $S^T$, producing the so-called "sensitivity-caused artifacts." As a consequence, the generated image seems to be directed toward the stronger side of sensitivity. This is why the reconstructed image based on Landweber technique has a better resolution near the wall (higher sensitivity) than the center region (lower sensitivity).

Other techniques based on Tikhonov regularization, simultaneous algebraic reconstruction technique (ART) and simultaneous iterative reconstruction technique (SIRT) are also widely used. Most techniques use a single criterion, i.e., least square error function. However, the lack of information concerning the nature of a "desirable" solution when the least square error is used alone does not necessarily give rise to an accurate image. More than one objective function is required to be considered simultaneously in order to choose the "best compromise solution" or the best probability of the answer among possible alternatives. This is especially true for 3D reconstruction, as the number of unknown voxel values is considerably increased with the same number of measurement data as in 2D reconstruction. The probability problem even worsens in the case of noise contaminated data. Increasing the number of electrodes will definitely increase the probability of obtaining a desirable solution. However, the maximum allowable number of electrodes is limited by the minimum possible electrode area and the signal to noise ratio. Multi-criterion optimization using more than one objective function than is needed to reduce the possibility of alternative solutions, and hence reducing the non-uniqueness of the problem in obtaining a more definitive solution. The implementation of more than one objective function yields a higher probability of obtaining an accurate solution (estimation) in the image reconstruction.

Multi-Criterion Optimization Image Reconstruction Technique (MOIRT)

Multi-Criterion Optimization Image Reconstruction Problem

A multi-criterion optimization based image reconstruction technique for solving the inverse problem of 2D ECT is extended to solve the inverse problem of the 3D ECT. The optimization problem finds the image vector that minimizes simultaneously the four objective functions: negative entropy function, least square errors, smoothness and small peakedness function, and 3-to-2D matching function. In addition to the least square error objective function, all the other functions involved in the reconstruction process collectively define the nature of the desired image based on the analysis of the reconstructed image. Thus, the error, which is generated from the linearized forward solver and propagated to the reconstructed image through the least square objective function, is minimized with the other objective functions applied. The negative entropy function, which should be minimized, is defined as in Equation 13:

$$f_1(G) = \gamma_1 \delta_1 G \ln G, \delta_1 = \{_{0 \, if \, G_j = 0}^{1 \, if \, G_j > 0} \quad (13)$$

Here, $\gamma_1$ is a normalized constant between 0 and 1. The least weighted square error of the capacitance measurement is defined in Equation 14:

$$f_2(G) = \frac{1}{2}\gamma_2 \|SG - C\|^2 \quad (14)$$

where S is the 3D sensitivity matrix with dimension of M by N, and M is the corresponding number of the measured capacitance data. $\gamma_2$ is normalized constant between 0 and 1. The smoothness and small peakedness function is defined as in Equation 15:

$$f_3(G) = \frac{1}{2}\gamma_3(G^T X G + G^T G). \quad (15)$$

Here X is N by N non-uniformity matrix. $\gamma_3$ is a constant between 0 and 1. An additional objective function for the 3D image reconstruction is required to match the 3D reconstructed image to the 2D, namely 3-to-2D matching function. which is defined in Equation 16 as:

$$f_4(G) = \frac{1}{2}\gamma_4 \|H_{2D} G - G_{2D}\|^2 \quad (16)$$

Here, $H_{2D}$ is projection matrix from 3D to 2D, having dimensions of $N \times N_{2D}$. $N_{2D}$ is the number of voxels in one layer of the 3D volume image vector G. $\gamma_4$ is a constant between 0 and 1. The 2D image vector is the 2D solution of the inverse problem in the image reconstruction. Finally, the multi-criteria optimization for the reconstruction problem is to choose an image vector for which the value of the multi-objective functions are minimized simultaneously.

Solution With Hopfield Neural Network

Hopfield and Tank proposed a technique based on a neural network model to solve optimization problem and in particular they presented a mapping of the traveling salesman problem onto neural networks. Since then, Hopfield neural networks model (or simply called Hopfield nets) has been used to successfully address a number of difficult optimization problems, including image restoration and image reconstruction for "hard field" tomography and "soft field" tomography. Their advantages over more traditional optimization techniques lie in their potential for rapid computational power when implemented in electrical hardware and inherent parallelism of the network.

To solve the image reconstruction problem, the image voxel value $G_j$ to be reconstructed is mapped into the neural output variable $v_j$ in the Hopfield nets. The output variable is a continuous and monotonic increasing function of the internal state of the neuron $u_j$ as shown in Equation 17:

$$G_j = v_j = f_\Sigma(u_j) \tag{17}$$

where $f_\Sigma$ is called activation function with typical choice of the form of Equation 18:

$$f_\Sigma(u_j) = [1 + \exp(-\beta u_j)]^{-1} \tag{18}$$

Here $\beta$ is a steepness gain factor that determines the vertical slope and the horizontal spread of the sigmoid-shape function. By using such a non-linear sigmoid-shape activation function, the neuron output is forced to converge between 0 and 1.

The behavior of a neuron in the network is characterized by the time evolution of the neuron state $u_j$ governed by the following differential Equation 19:

$$C_{0j} \frac{du_j}{dt} = -\frac{\partial E(G)}{\partial G_j} \tag{19}$$

where $C_{0j}$ is an associated capacitance in the j-th neuron, E(G) is the total energy of the Hopfield nets. The time constant of the evolution is defined by Equation 20:

$$\tau = R_{0j} C_{0j} \tag{20}$$

where $R_{0j}$ is the associated resistance. The overall energy function of the network includes a sum of the constraint functions (objective functions) to penalize violation of the constraints. The overall networks energy function corresponding to the optimization problem above becomes Equation 21:

$$E(G) = \sum_{i}^{4} w_i f_i(G) + \sum_{k=1}^{2} \Psi(z^k) + \sum_{j=1}^{N} \frac{1}{R_j} \int_0^{G_j} f_\Sigma^{-1}(G) dG \tag{21}$$

The first term in Equation 21 is the interactive energy among neurons based on the objective functions described above. The second term is related to the violation constraints (penalty functions) to the three weighted square error functions which must also be minimized. The third term encourages the network to operate in the interior of the N-dimensional unit cube ($0 \le G_j \le 1$) that forms the state space of the system. N is the number of neurons in the Hopfield nets, which is equal to the number of voxels in the digitized volume image. In the second term of Equation 21, where $z_{1,i} = SG - C$, $z_{2,i} = H_{2D}G - G_{2D}$. The constraint function $\Psi(\alpha_k z_k) = \Psi(\alpha_k z_{k,i})$ which is defined in Equation 22 as:

$$\frac{d\Psi}{dz_{k,i}} = \delta(\alpha_k z_{k,i}) = \begin{cases} 0 & \text{if } z_{k,i} \le 0_i \\ \alpha_k z_{k,i} & \text{if } z_{k,i} > 0 \end{cases} \quad (k,i,2,3) \tag{22}$$

Substituting all the objective functions in Equations 13 to 16 into Equation 22, the overall network energy function becomes Equation 23:

$$E(G) = \gamma_1 \delta_1 G \ln G + \frac{1}{2}\gamma_2 \|z_1\|^2 + \frac{1}{2}\gamma_3 (G^T X G + G^T G) + \tag{23}$$

$$\frac{1}{2}\gamma_4 \|z_2\|^2 + \Psi\{\alpha_1 z_1\} + \Psi\{\alpha_2 z_2\} + \sum_{j=1}^{N} \frac{1}{R_j} \int_0^G f_\Sigma^{-1}(G) dG$$

Equation 23 can be solved, for example, using Euler's method to obtain time evolution of the network energy. The form of penalty parameter $\alpha_k$ is chosen as Equation 24:

$$\alpha^k(t) = \alpha_0^k + \zeta^k \exp(-\eta^k t) \tag{24}$$

Here $\alpha_0^k$, $\zeta^k$ and $\eta^k$ are positive constants. The penalty parameter provides a mechanism for escaping local minima by varying the direction of motion of the neurons in such a way that the ascent step is taken largely by the penalty function in the initial steps. The value of the penalty factor reduces as the algorithm proceeds.

For simplicity, choosing $R_{0j} = R_0$ and $C_{0j} = C_0$, and defining $R_0 C_0$, $\gamma_1/C_0$ to $\gamma_4/C_0$ as $\tau$, $\gamma_1$ to $\gamma_4$, respectively, the time evolution of the internal state variable of neurons in the networks becomes Equation 25:

$$u'_j(t) = -\frac{u(t)}{\tau} - \gamma_1 W_1 \otimes \{1 + \ln G(t)\} - \tag{25}$$

$$\gamma_2 W_2 \otimes S^T z_1 - \gamma_3 W_3 \otimes \{XG(t) + G(t)\} -$$

$$\gamma_4 W_4 \otimes H_{2D}^T z_2 - S^T \delta(\alpha_1 z_1) - H^{2D,T} \delta(\alpha_2 z_2)$$

where $u'_j(t) = du_j(t)/dt, \ j = 1,2,3,\Lambda,N,$ $W_l = [w_{l1}, w_{l2}, \Lambda, w_{lN}]^T;$ $\sum_{l=1}^{4} w_{l,j} = 1; \ j = 1,2,\Lambda,N,$ $u(t) = [u_1(t), u_2(y), \Lambda, u_N(t)]^T,$ $G(t) = [G_1(t), G_2(t), \Lambda, G_N(t)]^T,$ $G_{2D}(t_\infty) = [G_{2D,1}(t_\infty), G_{2D,2}(t_\infty), \Lambda, G_{2D,N2D}(t_\infty)]^T$ $\otimes$ denotes an array multiplication (element-by-element product), and $t_\infty$, indicates the asymptotic solution of 2D image reconstruction using Hopfield network. The neuron state is updated as $u_j(t+\Delta t) = u_j(t) + u'_j(t) \Delta t$. The neuron output corresponds to the voxel value is updated as Equation 26:

$$v_j(t+\Delta t) = G_j(t+\Delta t) = f_\Sigma(u_j(t+\Delta t) = G_j(t) + f'_\Sigma(u_j(t)) u'_j(t) \Delta t \tag{26}$$

Here $f'_\Sigma(u) = df_\Sigma(u_j)/du$. The stopping rule is used when the changes in the firing rates become insignificant, i.e., for all voxels $|\Delta G(t)| \ll 1$.

Image Reconstruction Procedure

The first step is preprocessing by solving the 2D image matrices in Equation 16 using NN-MOIRT. The next step is initialization where the initial state of neurons is chosen as ($u_j$ (0)=0; $v_j$ (0)=$f_\Sigma$ ($u_j$ (0))). The steepness gain factor β is set to 2. The initial penalty parameter a and the initial gain factor ζ are the only parameters that significantly influence convergence performance and are obtained experimentally. Unless otherwise stated, $α_0$=50 and ζ=1.0 are used. The initial weights are $$w_1^{(0)} = w_2^{(0)} = w_3^{(0)} = w_4^{(0)} = \frac{1}{4}, \text{ and}$$

$$\gamma_1^{(0)} = \left[\sum_{j=1}^{N} G_j(0)\ln G_j(0)\right]^{-1},$$

$$\gamma_2^{(0)} = \left[\frac{1}{2}\|SG(0) - C\|^2\right]^{-1},$$

$$\gamma_3^{(0)} = \left[\frac{1}{2}G^T(0)XG(0) + \frac{1}{2}G^T(0)G(0)\right]^{-1},$$

$$\gamma_4^{(0)} = \left[\|H^{2D}G(0) - G_{2D}(t_\infty)\|^2 + \|H^{1D}G(0) - G_{1D}(t_\infty)\|^2\right]^{-1}$$

The next step is updating. The coefficients of the objective functions for every iteration step are calculated as follows:

$$\gamma_1^{(t+\Delta t)} = \left[\sum_{j=1}^{N} G_j(t)\ln G_j(t)\right]^{-1},$$

$$\gamma_2^{(t+\Delta t)} = \left[\frac{1}{2}\|SG(t) - C\|^2\right]^{-1},$$

$$\gamma_3^{(t+\Delta t)} = \left[\frac{1}{2}G^T(t)XG(t) + \frac{1}{2}G^T(t)G(t)\right]^{-1},$$

$$\gamma_4^{(t+\Delta t)} = \left[\|H^{2D}G(t) - G_{2D}(t_\infty)\|^2 + \|H^{1D}G(t) - G_{1D}(t_\infty)\|^2\right]^{-1}$$

And the weights $w_1$, $w_2$, $w_3$, $w_4$ for every iteration step are updated as follows:

$$w_i^{(t+\Delta t)} = \frac{\Delta w_1^{(t)}/\Delta w_i^{(t)}}{\sum_{i=1}^{4}\Delta w_1^{(t)}/\Delta w_i^{(t)}}, \Delta w_i^{(t)} = f_i(G(t + \Delta t)) - f_i(G(t)),$$

$$(i = 1,2,3,4)$$

where $f_1$~$f_4$ are objective functions in Equations 9 to Equation 12, respectively. The image vector is then updated using the iteration process in Equation 23. The updating procedure is repeated until the error is minimized.

The image reconstruction procedure is stopped when the termination scalar is determined to be |$G_j$ (t+Δt)−$G_j$ (t)|$^2$≤$10^{-4}$ for all neurons (voxels).

Sensor Design and Sensitivity Map

Figure 1B:
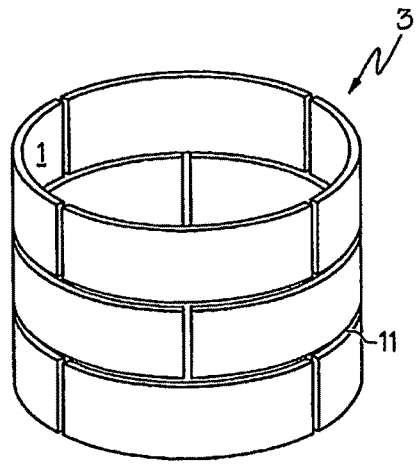

In two-dimensional ECT, the sensitivity matrix only has variation in radial (i.e., x- and y-axes) directions, assuming infinite length of the electrode in the z-direction. Imaging a three-dimensional object requires a sensitivity matrix with three-dimensional variation, especially in the axial (z-axis) direction to differentiate the depth along the sensor length. Therefore, the fundamental concept of the electrical capacitance sensor design for the 3D volume imaging is to distribute equally the electrical field intensity (sensitivity) all over the three-dimensional space (control volume) or with comparable electrical field intensity strength. This concept relates to the sensitivity variance (the difference between the maxima and minima) and the sensitivity strength (the absolute magnitude). Two sensor designs are described and their performances for 3D volume imaging evaluated, i.e., a 12-electrode triangular sensor arranged in one plane and a 12-electrode rectangular sensor arranged in triple planes as illustrated in FIGS. 1a and 1b. The triangular sensor in FIG. 1a comprises a triangular shape 1 electrode that forms six panels of two sensors 7 and 8.

The choice of the electrode number is based on the data acquisition system available which has 12 channels. However, the use of any other number of electrodes is possible. In addition, different shaped sensors, such as trapezoidal or any other shape or combination of different shapes, to enclose the 3D sensor region are also feasible as long as the sensor provides three-dimensional sensitivity distribution with relatively equal order of sensitivity strength or with comparable sensitivity strength. For example, for the rectangular sensor illustrated in FIG. 1b, the electrodes are arranged in three planes where each plane is shifted to another to distribute the electrical field intensity more uniformly in the axial direction and to increase the radial resolution up to twice the radial resolution of a 4-electrode sensor. The radial resolution of the rectangular sensor with this electrode arrangement, thus equals 8-electrode sensor per plane. However, the number of planes also can be greater than two to provide better variation in the axial direction. Additionally, for trapezoidal, triangular or any non-rectangular geometric shape sensors, it is also possible to use just a single plane.

Figure 2A:
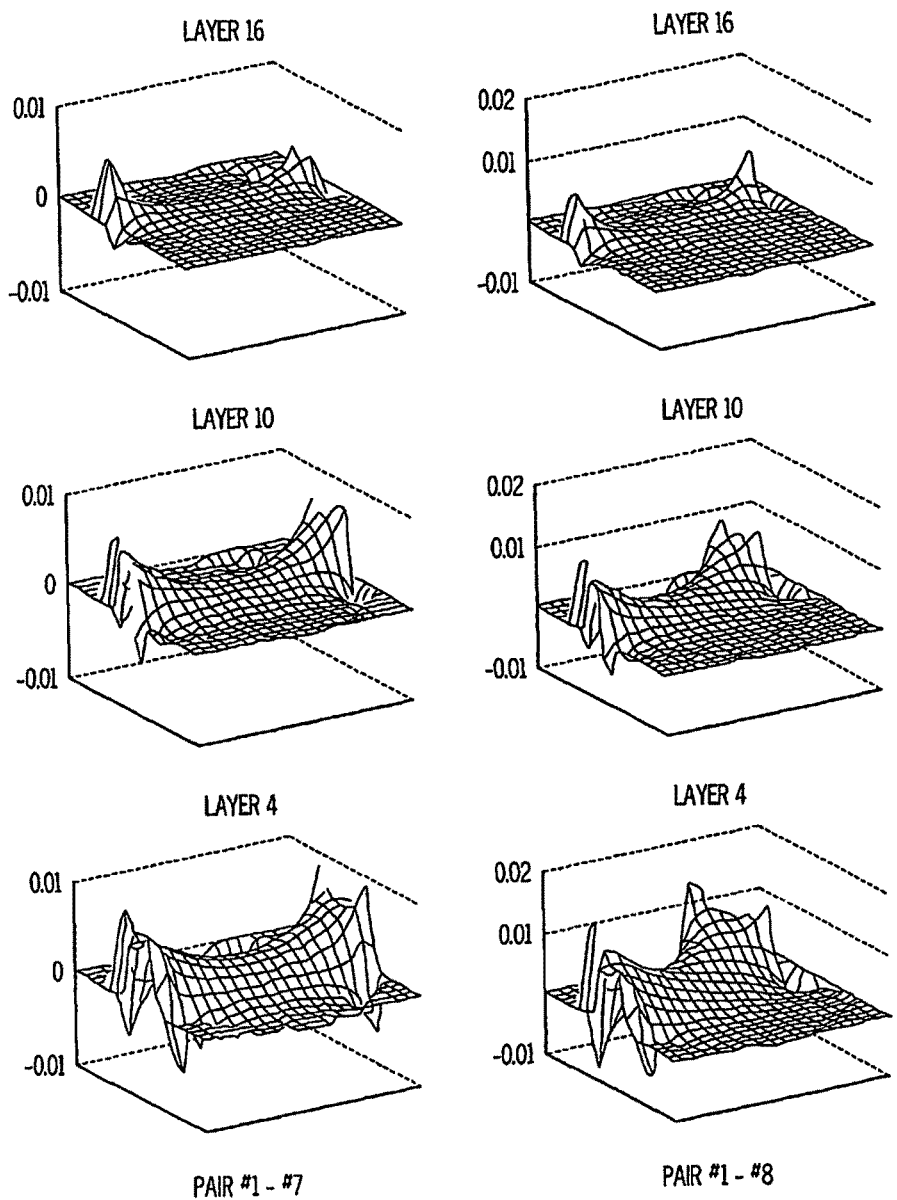
FIG. 2 illustrates three-dimensional sensitivity maps according to one embodiment of the present invention.
Figure 2B:
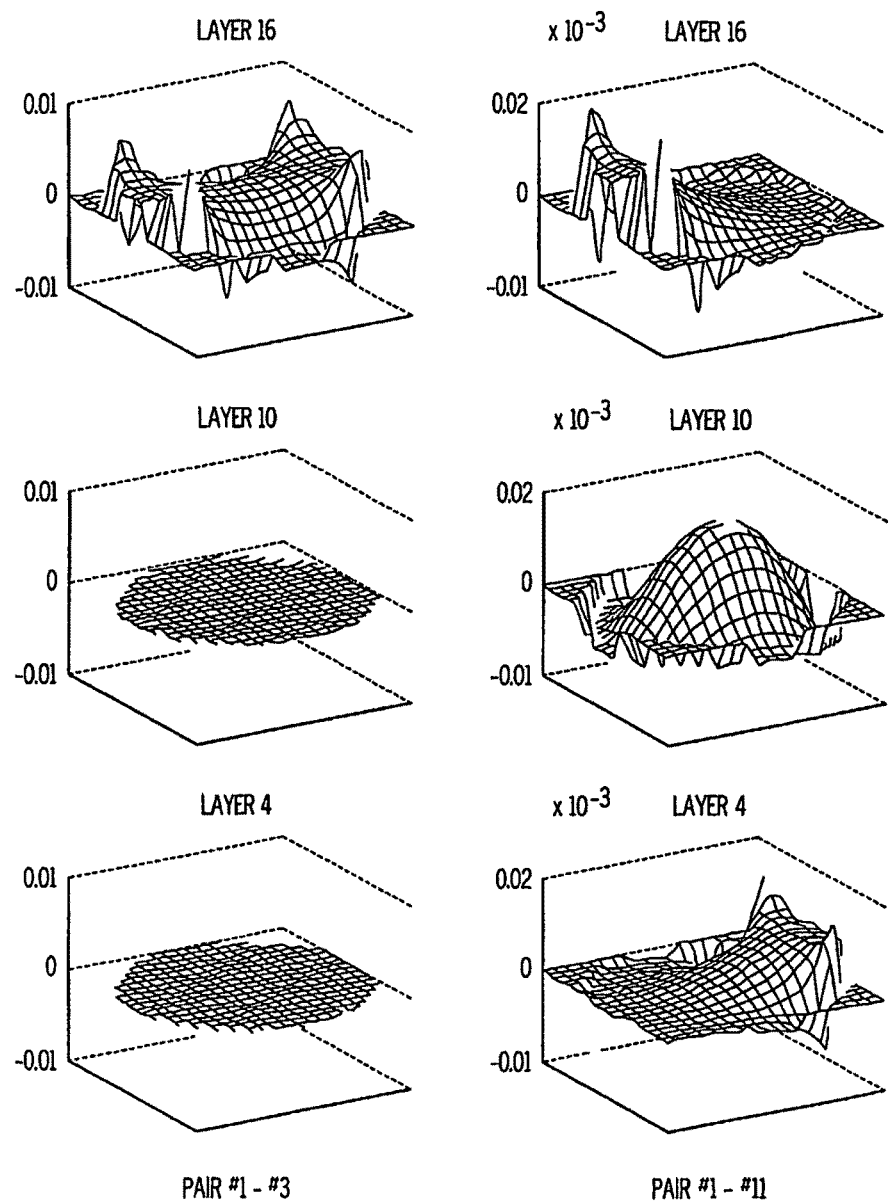

The sensitivity maps of the two capacitance sensors are illustrated in FIG. 2. The sensitivity maps show distributions of sensitivity variation in three-dimensional space. For the triangular sensor illustrated in FIG. 2(a), the sensitivity maps of capacitance readings between any electrode pair have a three-dimensional variation. On the other hand, it is only the sensitivity maps of capacitance readings between inter-plane electrode pairs that provide a three-dimensional variation in the rectangular electrode case as illustrated in FIG. 2(b). The maps show relatively comparable axial and radial sensitivity variation for the rectangular sensor, but less equally for the triangular sensor. Equal sensitivity variation all over the sensing domain is essential to avoid an artifact or image distortion in the reconstruction result due to inequality in the sensitivity strength distribution.

For the rectangular sensor, the largest magnitude in the sensitivity is found in the same-plane electrode pair capacitance reading, while the lowest is in the electrode pair between the first and third layers. The magnitude of the sensitivity strength does not affect significantly the image reconstruction process but it relates largely to the Signal-to-Noise Ratio (SNR) in the capacitance measurement. As seen in FIG. 2(b), the sensitivity strength in the first and third layers of electrode pairs is one order less in magnitude than that of the same-plane electrode pair. Therefore, the capacitance measurement between the first and third planes is very sensitive to noise. Therefore, the sensor requires very careful manufacture. The capacitance measurement between inter-plane electrode pair is related mostly to the horizontal length of the rectangular electrode, and is almost independent of the axial length of the electrode. Therefore, a consideration of the horizontal length of the electrode must be given in manufacturing the rectangular sensor.

Figure 3A:
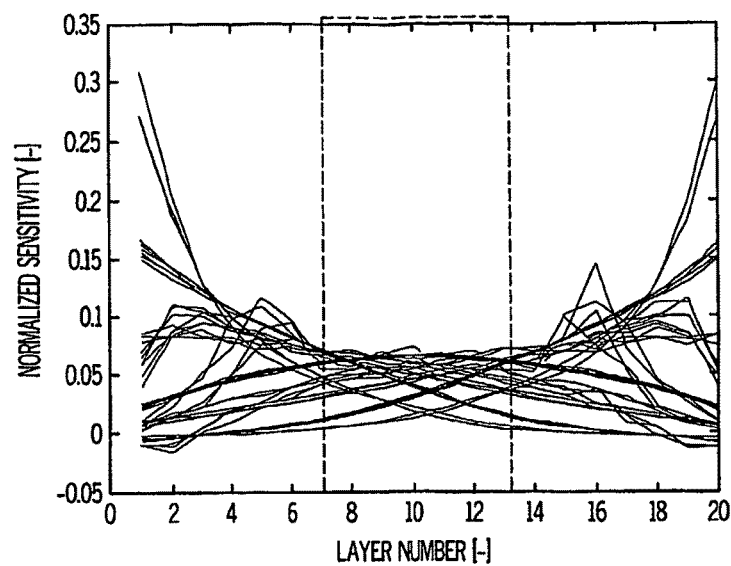
FIG. 3 illustrates axial sensitivity distribution for all capacitance readings according to one embodiment of the present invention.
Figure 3B:
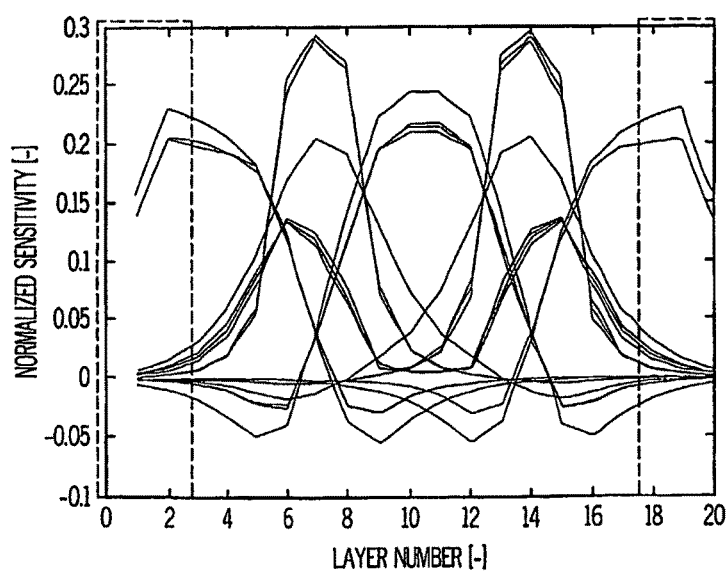

The sensor design and arrangement selected provides almost the same radial resolution over all the planes. Nevertheless, the axial resolution slightly differs in every plane. There are 66 combinations of independent capacitance measurements between the electrode pairs from the 12-electrode sensor systems. FIG. 3 illustrates the axial sensitivity distribution for all 66 electrode pairs for both sensors. Not much variation is observed for the triangular sensor in the middle of the sensing zone. This region gives no differentiation in the image reconstruction process and becomes a dead-zone in which a convergence is difficult to achieve. For the rectangular sensor, the dead zones are found in the bottom (layer numbers 1 to 3) and the top (layer numbers 18 to 20) portions of the sensor domain. The dead zones for the rectangular sensor can be removed by considering only the effective volume of the sensing domain, i.e., layers 4 to 17. All reconstructed images for the rectangular sensor, unless otherwise stated, belong to the effective sensor domain.

A dual sensitivity matrix (capacitance plus power measurement data) can be constructed and used for solving both forward and inverse problems. The dual matrix elements are approximated based on the electric field distribution in the empty sensor scenario.

The difference in capacitance is related directly to the difference in total stored energy caused by the permittivity pixel. This energy difference is composed of two components: internal to the pixel $\Delta W_{int}$ and external to the pixel $\Delta W_{ext}$. The constants $\beta_{int}$ and $\beta_{ext}$ are introduced to simplify the final equations. Combining both energy components, we have:

$$\Delta C = \frac{2}{(\Delta V)^2}(\beta_{ext} + \beta_{int})|\vec{E}_0|^2, \tag{27}$$

Hence, the capacitance difference introduced by a small perturbation in permittivity is proportional to the square of the unperturbed electric field (empty vessel). Thus, in order to solve for the sensitivity matrix, the sensor model has to be solved once in the empty case.

Similarly to the capacitance matrix, each element in the power matrix linearizes the relation between the conductive (heating) loss and a small conductive pixel perturbation in an insulating background given by 3, integrated over the (small) pixel volume having conductivity.

Based on these results, the power sensitivity matrix elements are approximated as follows:
1) Diffusion-dominated regime ($\sigma \gg \omega\varepsilon$): matrix elements are approximated as in Equation 28.
2) Diffusion-dominated regime ($\sigma \ll \omega\varepsilon$): matrix elements are approximated as in Equation 29.
3) Mixed regime ($\sigma \approx \omega\varepsilon$): matrix elements are approximated as in Equation 30.

$$P = \frac{1}{2}\left(\frac{4}{3}\pi r^3\right)(\sigma)\left(|\vec{E}_0|\frac{10^{-3}}{\sigma}\right)^2, \tag{28}$$

$$P = \frac{1}{2}\left(\frac{4}{3}\pi r^3\right)(\sigma)\left(|\vec{E}_0|\frac{1.88}{\varepsilon_r}\right)^2, \tag{29}$$

$$P = \frac{1}{2}\left(\frac{4}{3}\pi r^3\right)(\sigma)\left(|\vec{E}_0|\frac{1}{|\sigma + j\omega\varepsilon|}\right)^2, \tag{30}$$

In all three regimes above, the dissipated power inside the pixel is calculated based on the electric field in the empty sensor case. Thus, the same field solution used for calculating the capacitance sensitivity matrix can be used here for calculating the power sensitivity matrix.

Experiment

Figure 1C:
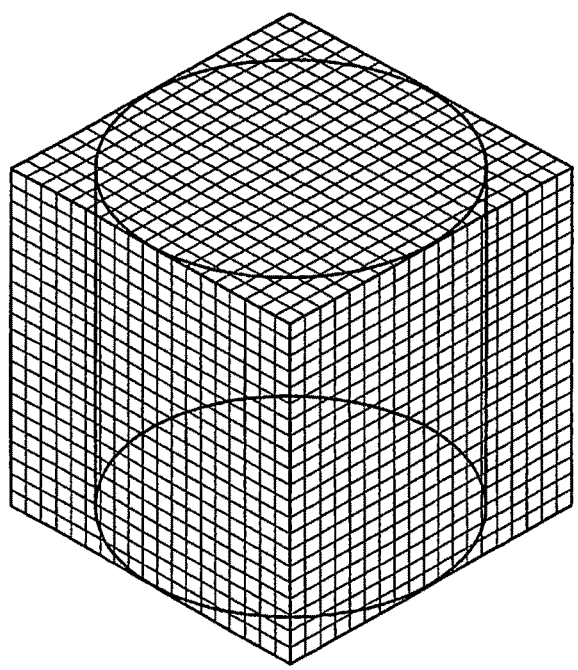

A 12-channel data acquisition system (DAM200-TP-G, PTL Company, UK) can be used. The ECT system comprises a capacitance sensor, sensing electronics for data acquisition and a processing system for image reconstruction. The sensors can include two types of 12-electrode systems as illustrated in FIG. 1. The length of the sensing domain of the capacitance sensor can be about 10 cm with a column diameter of about 10 cm. The data acquisition system can be capable of capturing image data up to about 80 frames per second. The test object is a dielectric sphere with an internal diameter of about ¼ the column internal diameter and a relative permittivity=3.8. The image is reconstructed on a 20×20×20 resolution based on the algorithm described above. The volume image digitization is illustrated in FIG. 1c.

An ECT sensor was used to assess the multimodal tomography system performance. The sensor operates at about 10 MHz. Simulations for sensitivity calculations and boundary measurements can be carried out using FEM. A dual sensitivity matrix for capacitance and power perturbations was constructed based on the electric field solution of the sensor in its empty state. The reconstruction process, data forward simulations, and data post-processing can be processed on a Pentium IV computer, with a 3 GHZ processor and with a 3 GB RAM memory.

Reconstruction Result

Figure 4A:
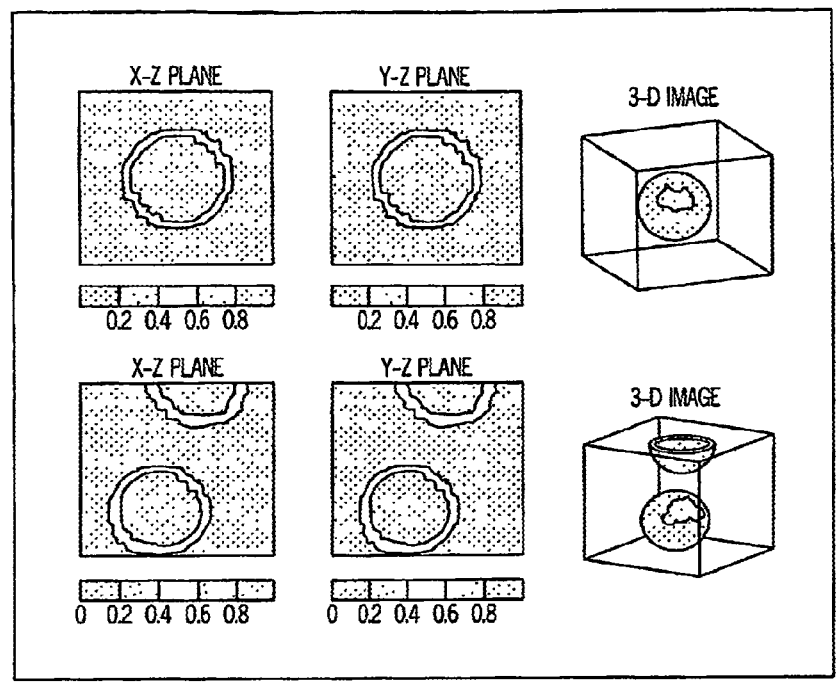
FIG. 4A illustrates reconstruction results for a sphere object using NN-MOIRT according to one embodiment of the present invention.
Figure 4B:
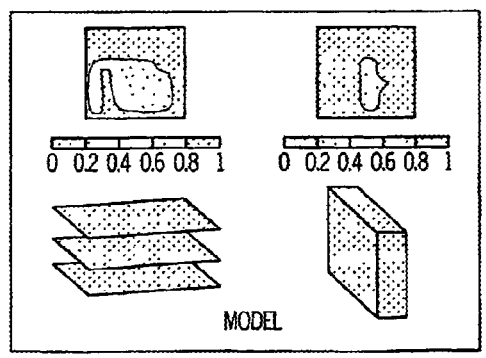
FIG. 4B illustrates reconstruction results for a sphere and one half of a sphere using NN-MOIRT according to one embodiment of the present invention.
Figure 4C:
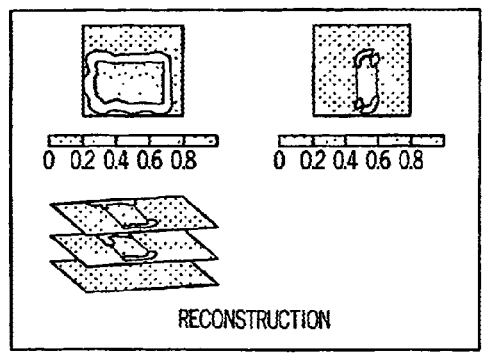
FIG. 4C illustrates reconstruction results for a dielectric block using NN-MOIRT according to one embodiment of the present invention.

FIG. 4 illustrates the three-dimensional reconstruction results of a dielectric sphere, a one and half sphere and a dielectric block based on simulated capacitance data using NN-MOIRT algorithms. The diameters of both spheres are half the diameter of the sensor equaling the whole dimension of the image. The sensor used was a 12-electrode twin-plane triangular sensor. Excellent agreements between the reconstructed 3D images and the model images were obtains for all images.

Figure 5:
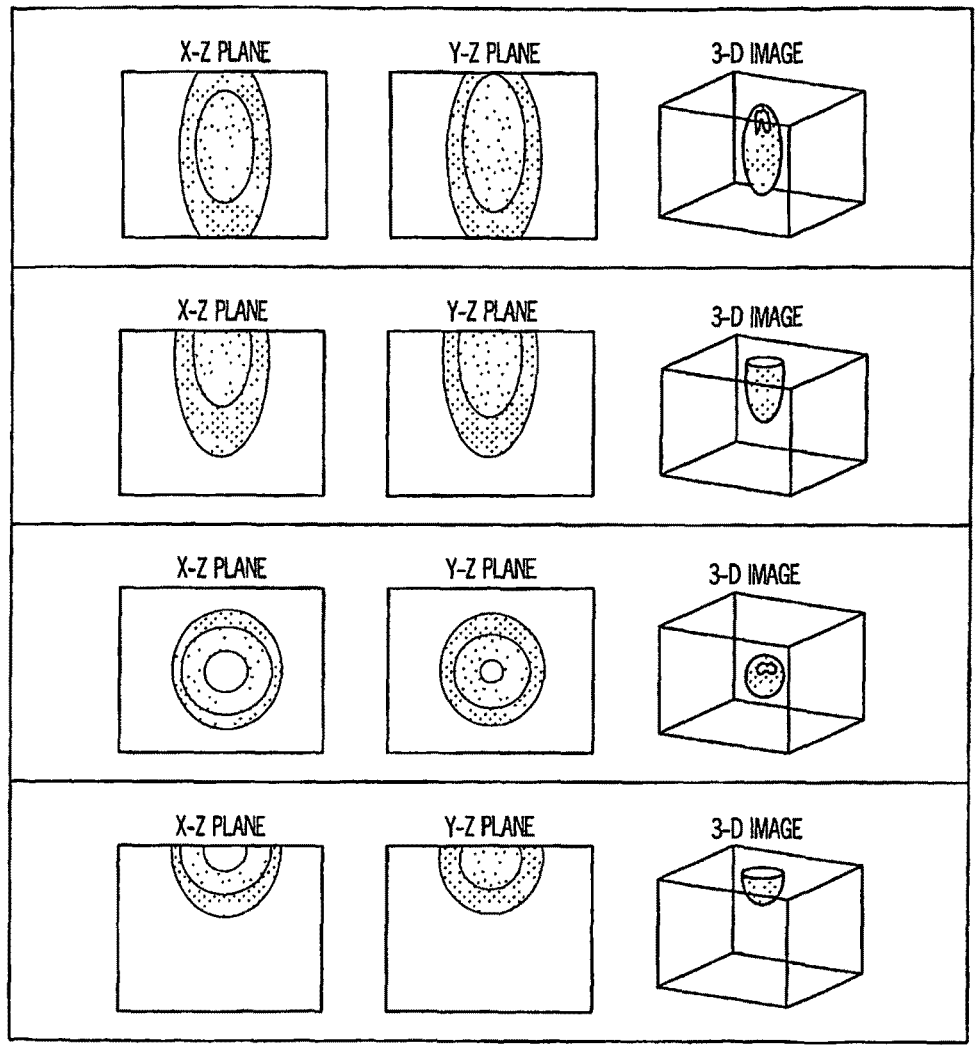
FIG. 5 illustrates reconstruction results for a sphere in the center and the edge of sensing domain using the LBP technique according to one embodiment of the present invention.
Figure 6:
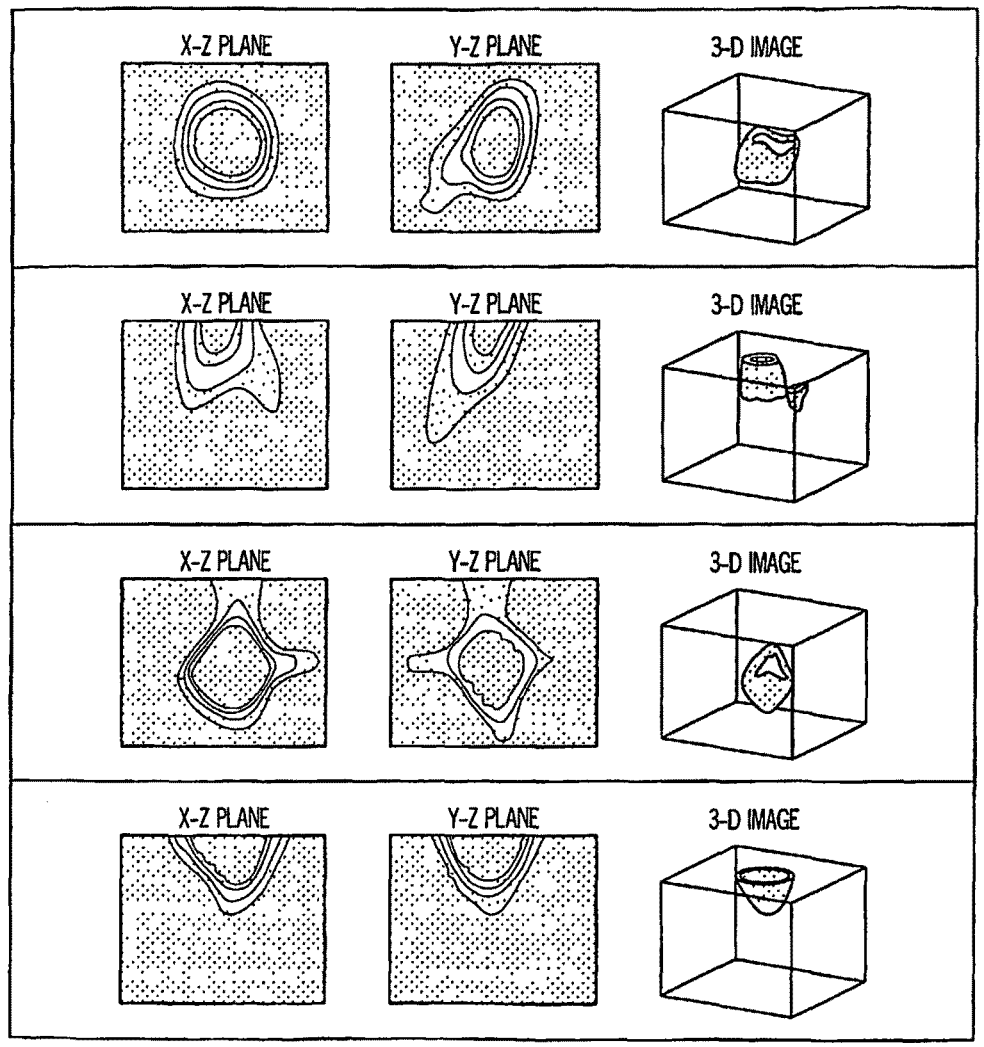
FIG. 6 illustrates reconstruction results for a sphere in the center and the edge of sensing domain using the Landweber technique according to one embodiment of the present invention.
Figure 7:
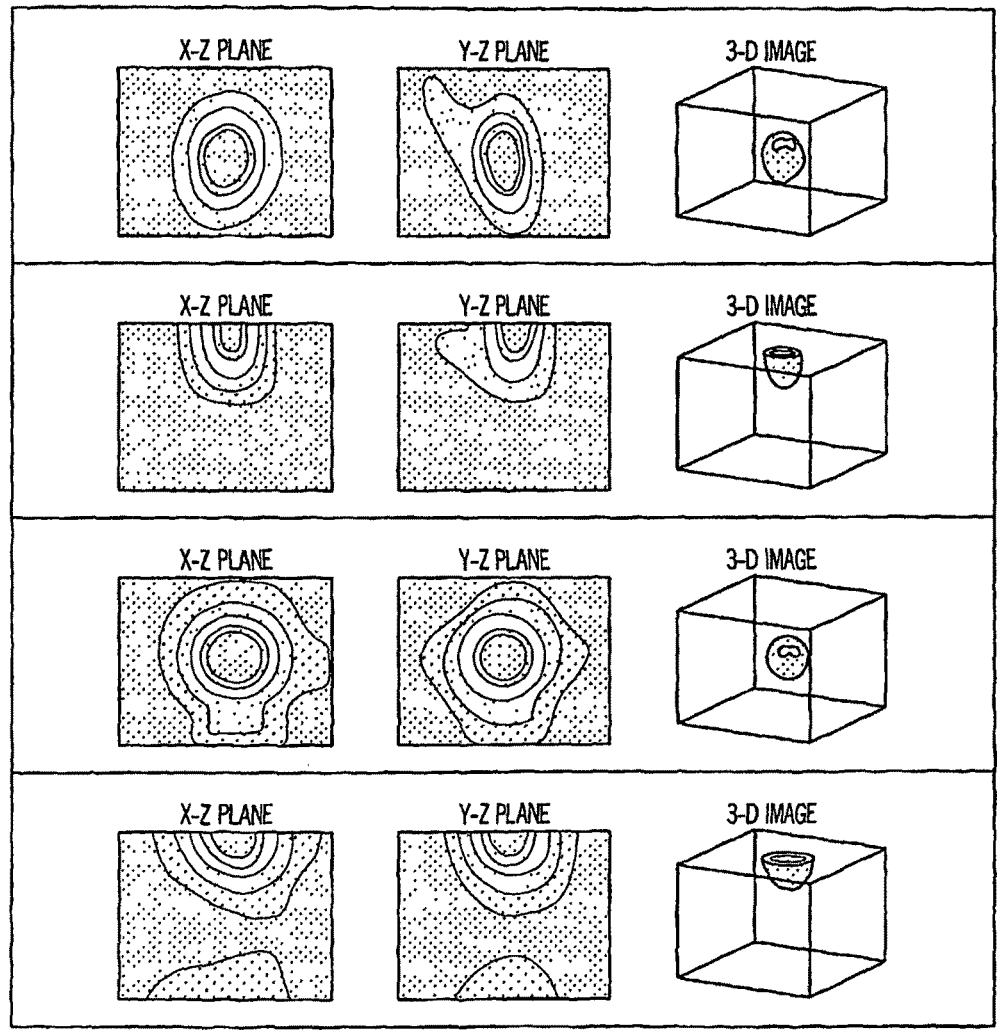
FIG. 7 illustrates reconstruction results for a sphere in the center and the edge of sensing domain using NN-MOIRT according to one embodiment of the present invention.

The reconstruction results from measurement data are shown in FIGS. 5-7 using the two electrode designs illustrated in FIG. 1 and the three reconstruction algorithms: LBP, Landweber (or ILBP), and NN-MOIRT. The iteration number was set to 100 in all cases. The reconstructions are based on actual capacitance measurements of dielectric objects: one sphere located in the center of the sensing domain and another sphere located half inside the sensing domain. Each row in every figure contains two slice images of X-Z and Y-Z cuts in the first two columns and one 3D image in the third column. The 3D image can be an isosurface display with an isovalue of half of the maximum permittivity.

FIG. 5 illustrates the reconstruction results on the LBP technique. Elongation in axial direction of the reconstructed images occurs to both the objects for the single-plane triangular sensor. The axial elongation effect is expected as the sensitivity variation in the axial direction for the triangular electrode is insignificant as compared to that in the radial direction (see FIG. 3a). For the rectangular sensor (FIGS. 5c and d), the technique gives relatively accurate shapes of the objects through a smoothing effect appears in the sharp boundary of the reconstructed images. The contrasts between low and high permittivity regions in the reconstructed images are relatively uniform in both radial and axial direction. The conserved shape and the uniform contrast in the reconstructed image are largely due to the sensitivity variation and thus spatial resolution, corresponding to the electrode design. This result indicates that the triple-plane rectangular electrode gives relatively more uniform sensitivity variation in both the radial and axial directions as compared to the single-plane triangular sensor.

FIG. 6 illustrates the reconstruction results for the Landweber technique (or iterative LBP). The reconstructed images are severely distored in all cases for both sensor designs. An elongation effect is also observed for the triangular sensor. The reconstructed images appear to be directed toward the sensing sites with relatively stronger sensitivities, which correspond to the junctions between electrodes, causing a distortion and elongation due to a "sensitivity-caused artifact" as described above. The distortion may also arise from noises contained in the capacitance data.

The reconstructed volume images using the NN-MOIRT algorithm are illustrated in FIG. 7. For the triangular sensor, although the elongation effect is still observed, the results are much better compared to those using LBP and Landweber techniques. The effect of noise to the reconstructed image is also minimal as compared to the Landweber technique. For the rectangular sensor, the reconstructed images are almost perfect except for the contrast which is less clear as compared to the triangular sensor. By using a rectangular sensor arranged in three planes, thereby increasing sensitivity variation in the axial direction, the elongation problem caused by a non-uniform sensitivity strength between the axial and radial directions can be resolved. However, with the same number of electrodes in the triangular sensor, the spatial resolution for the rectangular electrode is decreased, resulting in less contrast in the reconstructed image. Increasing the number of electrodes per plane for the rectangular sensor can increase the contrast between low and high permittivities in the reconstructed image.

Figure 9:
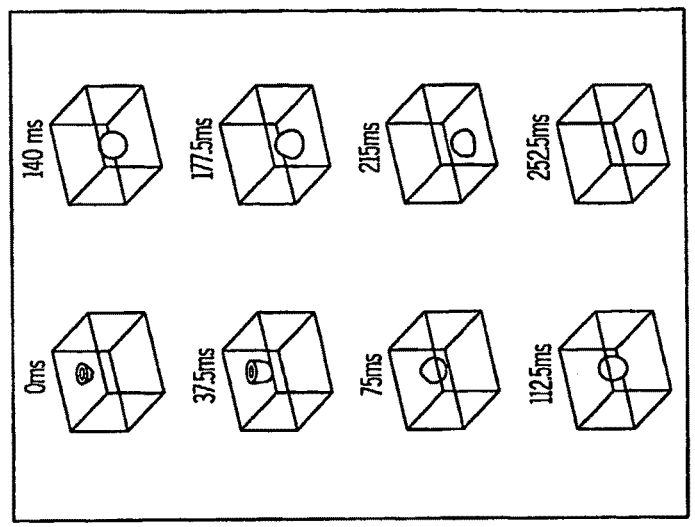
FIG. 9 illustrates a 3D image of a falling sphere reconstructed using NN-MOIRT according to one embodiment of the present invention.
Figure 8:
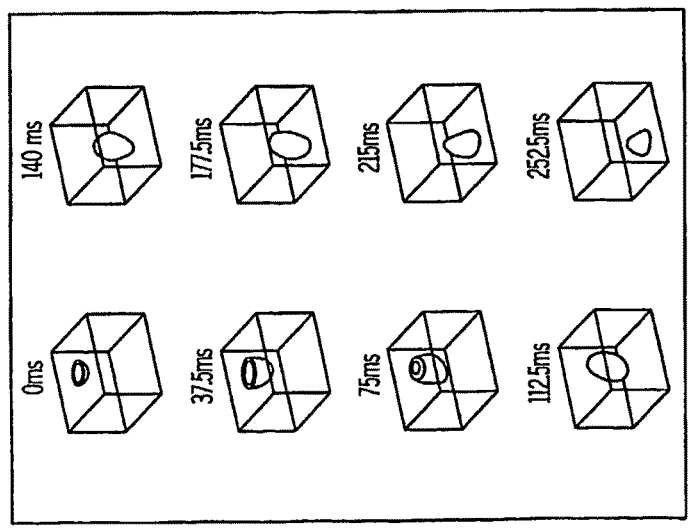
FIG. 8 illustrates a 3D image of a falling sphere reconstructed using the Landweber technique according to one embodiment of the present invention.

FIGS. 8 and 9 show a series of instantaneous volume-image of the same dielectric sphere used in FIG. 5-7 when falling through the inside of the sensor based on image reconstruction results using the Landweber technique and NN-MOIRT. A distortion in the shape of the reconstructed images from level to level is observed in the Landweber technique results. On the other hand, the shape of the reconstructed images using NN-MOIRT is relatively conserved at every level, verifying the capability of the algorithm to resolve, to some extent, the effect of "sensitivity-cause artifact." This result also indicates that the technique requires fewer measurement data to generate the same image quality as produced by the Landweber technique. The capability to minimize the effect of "sensivity-caused artifact" is essential, in particular for volume imaging, as there will always be non-uniformity in the sensitivity strength due to the 'soft field" effect. The use of entropy function and the distribution of the weight coefficients to the different objective functions are considered to be effective in minimizing the effect of "sensitivity-caused artifact." Both factors are unique to the NN-MOIRT algorithm. Distribution of weight coefficients is made in such a way to provide a uniform speed of convergence in each voxel.

Figure 10:
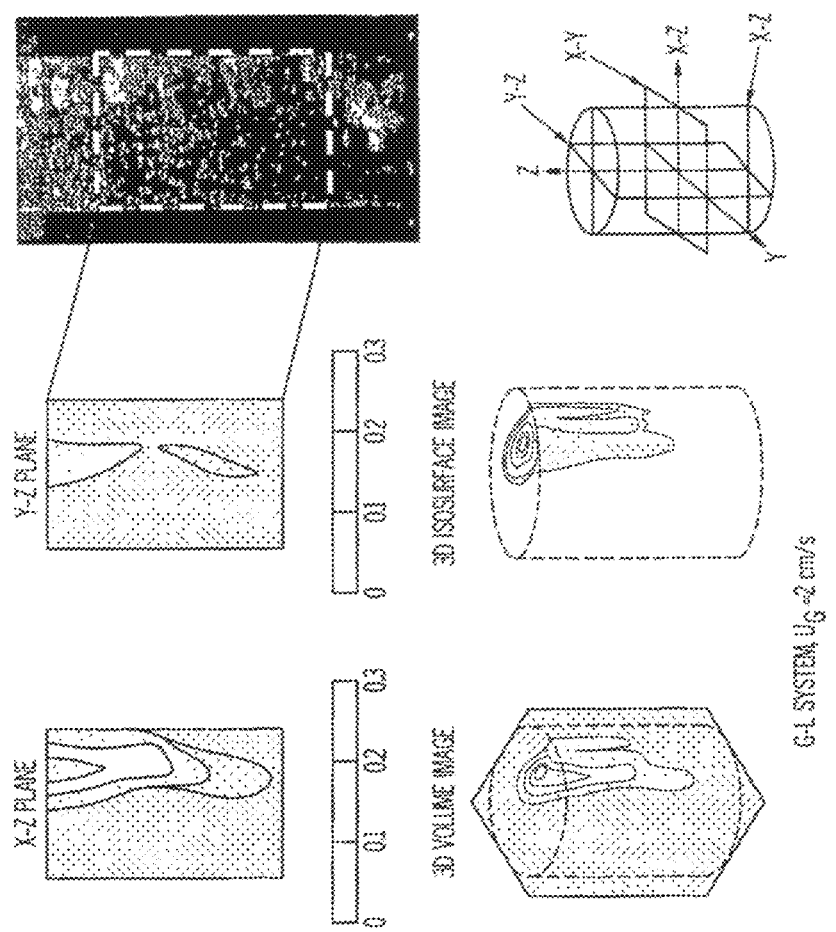
FIG. 10 illustrates snapshots of 3D volume images of gas-liquid flow in a bubble column according to one embodiment of the present invention.
Figure 11:
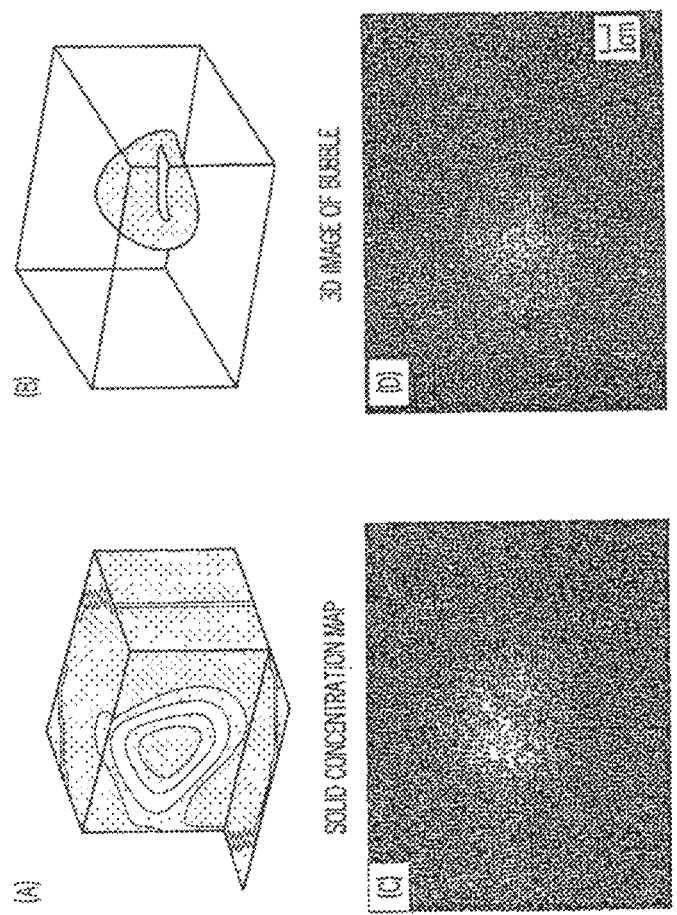
FIG. 11 illustrates snapshots of volume image of bubble in gas-solid fluidized bed using group B particles according to one embodiment of the present invention.

One example of application result of the technique for multiphase flow imaging of gas-liquid flow in a vertical column in illustrated in FIG. 10 which shows a snapshot of the tomography volume image (3D gas concentration distribution) of the multiphase flow. The tomography volume image is constructed from permittivity voxel values in 4D matrix components, i.e., three space components with spatial resolution of 5×5×8 mm³ and one time component with a temporal resolution of 12.5 ms. The voxel permittivity values are converted into phase concentration (holdup) of the multiphase system based on the capacitance model described above. The first two figures in the top row are slice cut images of the planes defined by the coordinate system in the bottom-right in the figure. The first and second figures in the bottom row are, respectively, a 3D volume image which is partly cut-off to display the inside of the 3D representation and a 3D isosurface image which displays the 3D boundary (surface) of the bubble swarm image. The cut-off boundary value was set at 10% of the gas holdup value. The cut-off boundary selection was arbitrary and used to provide some sense of distinction of the boundary of high-concentration bubble swarm from the surrounding low gas concentration region. For comparison with the tomography images, a photograph of the two-phase flow was taken using a high-speed digital video camera under the same conditions is displayed on the right-hand side of the figure, An example of the application result of the technique for multiphase flow imaging of gas-solid flow in a vertical column is illustrated in FIG. 11, showing a well-known apple shape image of a bubble in gas-solid fluidization system as compared with a 1D X-ray photograph. The image confirms the accuracy and quickness in real-time volume-imaging of moving dielectric objects.

Figure 12A:
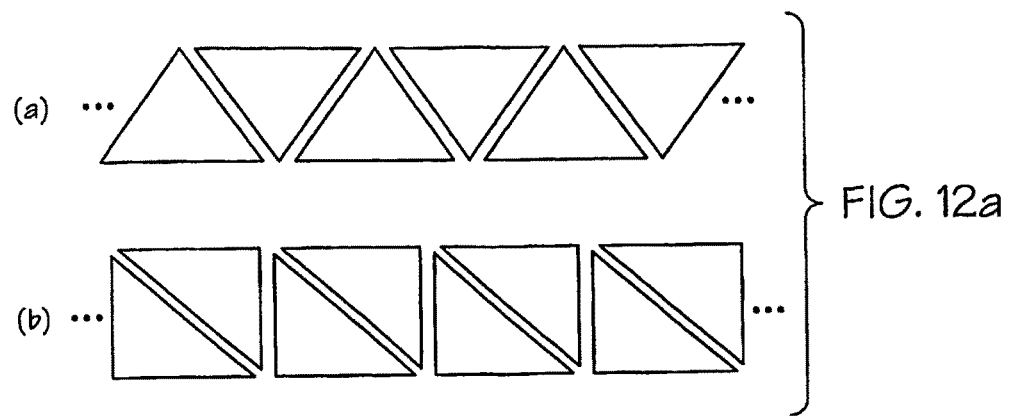
FIG. 12 illustrates different electrode designs according to one embodiment of the present invention.
Figure 12B:
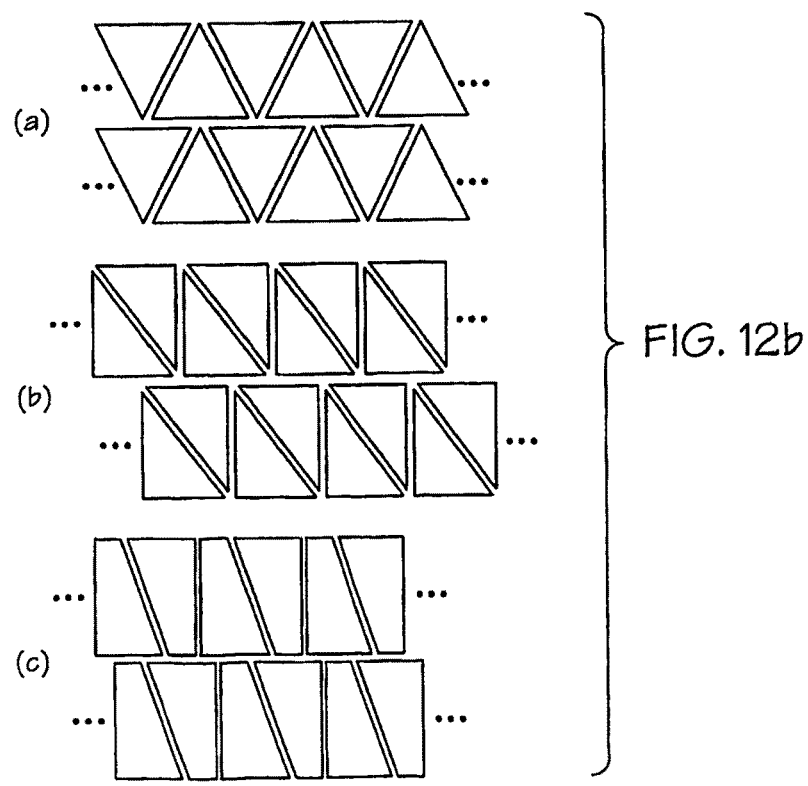
Figure 12C:
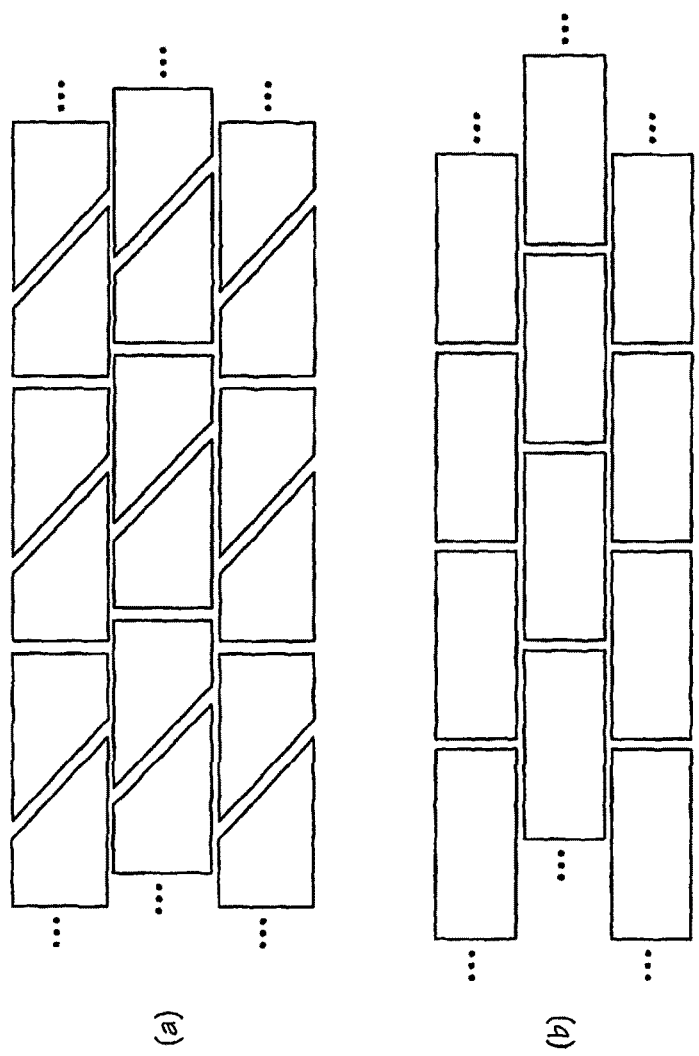
Figure 13A:
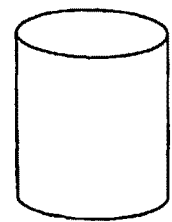
FIG. 13 illustrates different capacitance sensor designs for ECVT applications according to one embodiment of the present invention.
Figure 13B:
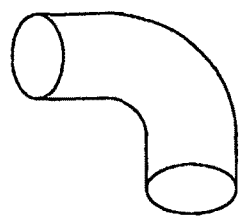
Figure 13C:
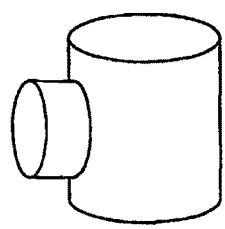
Figure 13D:
Figure 13E:
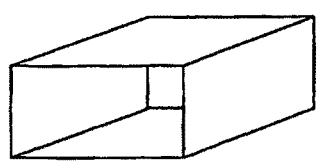
Figure 13F:
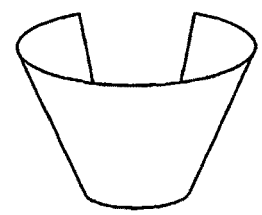

FIGS. 12(a-c) illustrate different designs of capacitance electrodes selected based on different shapes of control volume and imaging purposes. For example, the technique is feasible for volume imaging of multiphase systems in conduits such as pipe bends, T-junctions, conical vessels or other complex geometrical systems shown in FIG. 13. The technique is open possible for real time 3D medical imaging of the human body as well as for the real time monitoring of tablet manufacturing in the pharmaceutical industry.

As discussed above, the "soft field" nature and ill-posedness of the inverse problem are the main problems encountered in the reconstruction process. Iterative linear back projection (ILBP) is used for image reconstruction for the multimodal tomography system. In ILBP, both forward and inverse problems are solved iteratively to minimize the residual image error. In contrast to traditional ILBP based on a single modality sensitivity matrix, a dual modality sensitivity matrix is used here. The first component of the matrix represents the capacitance perturbation, whereas the second component refers to the conductivity perturbation. In ILBP, the image vector is updated iteratively to minimize the error between measured and calculated integral measurement data according to:

$$G^{k+1} = G^k + \tau(S^T(M-SG^k)), \tag{31}$$

where the calculated boundary value is obtained from the reconstructed image using linear forward projection. In the above, G is the image vector, k is the iteration number, S is the sensitivity matrix, τ is a factor controlling reconstruction convergence, and M is the boundary measurement.

Figure 14:
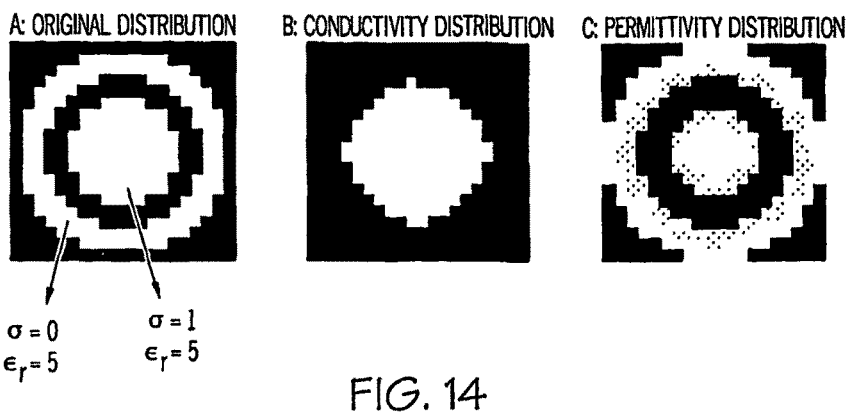
FIG. 14 illustrates reconstruction of the simulated data for the diffusion case in multimodal tomography according to one embodiment of the present invention.
Figure 15:
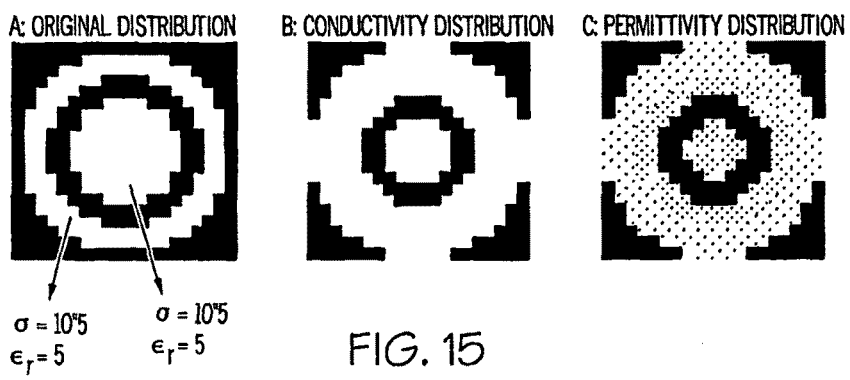
FIG. 15 illustrates reconstruction of simulated data for the conviction case in multimodal tomography according to one embodiment of the present invention.

Reconstruction results for diffusion- and convection-dominated cases are presented in FIGS. 14 and 15 respectively. In FIG. 14, the high value of conductivity constant in the center region enables the solution to converge to two distinct regions of permittivity and (pure) conductivity maps. In FIG. 15, the electrical field distribution is mainly controlled by the permittivity constant due to relatively small values of conductivity. As a result, the permittivity reconstruction captures both the center and ring distributions. The conductivity reconstruction, on the other hand, is able to reconstruct the center conductive region satisfactorily. Thus, in the case of both convection and diffusion-dominated cases, an independent reconstruction of permittivity and conductivity can be implemented.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A system for generating a three-dimensional tomograph of a vessel interior or other object, the system comprising:
   a three-dimensional capacitance sensor device comprising a plurality of electrodes for placement around the vessel or the object, wherein the three-dimensional capacitance sensor device is adapted to provide electric field distribution and sensor sensitivity in three geometric dimensions;
   data acquisition electronics in communication with the three-dimensional capacitance sensor device for receiving input data from the three-dimensional capacitance sensor device;
   a processing system in communication with the data acquisition electronics, the processing system programmed with instructions for executing on the processing system to reconstruct a three-dimensional volume-image from the input data collected by the data acquisition electronics.

2. A system according to claim 1, wherein the electrodes of the three-dimensional capacitance sensor device are triangular or trapezium in shape.

3. A system according to claim 1, wherein the three-dimensional capacitance sensor device is comprised of at least two planes of electrodes to provide sensor sensitivity in the axial and radial directions.

4. A system according to claim 1, wherein the processing system is programmed with an image reconstruction algorithm.

5. A system according to claim 4, wherein the image reconstruction algorithm is adapted to provide real-time imaging of multiphase flow within the vessel.

6. A system according to claim 1, wherein the processing system is programmed to calculate capacitance data from the input data received by the data acquisition electronics.

7. A system according to claim 1, wherein the object is a human body.

8. A system according to claim 1, wherein the processing system is programmed with instructions to: 1) convert a three-dimensional image into an image vector, wherein elements of the image vector are voxels of the three-dimensional image; 2) define a three-dimensional sensitivity matrix related to the image vector and based on geometry of the geometrically three-dimensional capacitance sensor device and a matrix of measured capacitance; 3) compute a volume image vector using a reconstruction algorithm selected based on the three-dimensional sensitivity matrix and matrix of the measured capacitance; and 4) convert the volume image vector to the three-dimensional volume-image.

9. A system according to claim 1, wherein the three-dimensional capacitance sensor device is comprised of a plurality of rectangular electrodes arranged in a triple plane configuration.

10. A system according to claim 1, wherein the three-dimensional capacitance sensor device is any shape or arrangement of electrodes that provides a three-dimensional electric field intensity in three directions with substantially equal strength.

11. A system according to claim 1, wherein the plurality of electrodes are arranged in one plane with nonrectangular-shaped electrodes for providing electric field distribution and sensor sensitivity in the radial and axial direction.

12. A system according to claim 1, wherein the system including the three-dimensional capacitance sensor device is adapted to simultaneously measure variations in both capacitance and power corresponding to permittivity and conductivity distribution.

13. A system according to claim 1, further comprising a dual capacitance/power sensitivity matrix obtained by the three-dimensional capacitance sensor device.

14. A system according to claim 1, further comprising:
   a time varying driving signal for use as an excitation signal for the system.

15. A system according to claim 1, wherein a three-dimensional imaging domain of the three-dimensional capacitance sensor device is divided into voxels and wherein the data acquisition electronics receives data for each voxel and wherein the processing system is programmed with instructions for executing on the processing system for reconstructing the three-dimensional volume-image based on the data received for each voxel.

16. A system according to claim 1, wherein the system is adapted to distribute electric field intensity or sensor sensitivity substantially equally within the three-dimensional capacitance sensor device.

17. A system according to claim 1, wherein the processing system is programmed with instructions for executing on the processing system for providing a multi-criterion optimization based image reconstruction technique.

18. A system according to claim 1, wherein the system including the three-dimensional capacitance sensor device is adapted to obtain both capacitance and impedance flow information.

19. A system according to claim 1, wherein there are N number of electrodes and wherein the system is programmed to collect $N(N-1)/2$ capacitance measurements for all of the combinations of electrode pairs for use in volume-image reconstruction, and wherein the three-dimensional capacitance sensor device is comprised of at least two planes of electrodes in the axial direction to provide sensor sensitivity in the radial and axial directions.

20. A system according to claim 1 wherein the system provides substantially equal sensor sensitivity over the entire sensing domain of the three-dimensional capacitance sensor device.

21. A system for generating a three-dimensional tomograph of a vessel interior or other object, the system comprising:
   a three-dimensional capacitance sensor device comprising a plurality of electrodes for placement around the vessel or the object, wherein the three-dimensional capacitance sensor device is adapted to provide electric field distribution and sensor sensitivity in three geometric dimensions;

data acquisition electronics in communication with the three-dimensional capacitance sensor device for receiving input data from the three-dimensional capacitance sensor device; and a processing system in communication with the data acquisition electronics, the processing system programmed with instructions for executing on the processing system to reconstruct a three-dimensional volume-image from the input data collected by the data acquisition electronics; and wherein the three-dimensional capacitance sensor device is comprised of at least two rows or planes of electrodes to provide sensor sensitivity in the radial and axial directions.

22. A system according to claim 21, wherein each of the plurality of electrodes are connected to a channel of the data acquisition electronics and wherein there are an N number of electrodes and the system is adapted to take N(N−1)/2 capacitance measurements for each electrode pair.

23. A system according to claim 22, wherein the processing system is programmed with instructions for executing on the processing system to reconstruct the three-dimensional volume-image from the actual capacitance measurements collected by the data acquisition electronics without the need for averaging.

24. A system according to claim 23, wherein the system provides substantially equal sensitivity variation over the sensing domain of the three-dimensional capacitance sensor device.

25. A system according to claim 21, wherein a three-dimensional imaging domain of the three-dimensional capacitance sensor device is divided into voxels and wherein the data acquisition electronics receives data for each voxel and wherein the processing system is programmed with instructions for executing on the processing system for reconstructing the three-dimensional volume-image based on the data received for each voxel.

26. A system according to claim 21, wherein the arrangement of the plurality of electrodes or the shape of the plurality of electrodes can be changed to vary the sensor sensitivity.

27. A system according to claim 21, wherein a sensitivity matrix of the three-dimensional capacitance sensor device has a dimension of (M×N), where M is the number of electrode pair combinations and N is the number of voxels.

28. A system according to claim 21, wherein the system is adapted to distribute electric field intensity or sensor sensitivity substantially equally within the three-dimensional capacitance sensor device.

29. A system according to claim 21, wherein the processing system is programmed with instructions for executing on the processing system to eliminate data collected from regions of the three-dimensional capacitance sensor where electric field or sensor sensitivity is substantially negligible.

30. A system according to claim 21, wherein the system is adapted to provide sensor sensitivity between a first and second plane of electrodes.

31. A system according to claim 21, wherein the system is adapted to provide sensor sensitivity between at least one pair of electrodes from a first and second plane of electrodes.

32. A system according to claim 21, wherein the at least two rows of electrodes are formed by one plane of electrodes of nonrectangular shape.

33. A system according to claim 21, wherein the three-dimensional capacitance sensor device is adapted to provide interrogation of the whole volume of an imaging domain of the three-dimensional capacitance sensor device and wherein the processing system is programmed with instructions for executing on the processing system for reconstructing the three-dimensional volume-image of the vessel interior or other object based on the interrogation of the whole volume of the imaging domain.

34. A system according to claim 33, wherein the processing system is programmed with instructions for executing on the processing system for providing real-time volume imaging.

35. A system according to claim 21, wherein the three-dimensional capacitance sensor device is of irregular shape.

36. A system according to claim 21, wherein the three-dimensional capacitance sensor device partially encloses the vessel or the object.

37. A system for generating a three-dimensional tomograph of a vessel interior or other object, the system comprising:

a three-dimensional capacitance sensor device comprising a plurality of electrodes for placement around the vessel or the object, wherein the three-dimensional capacitance sensor device is adapted to provide electric field distribution and sensor sensitivity in three geometric dimensions;

data acquisition electronics in communication with the three-dimensional capacitance sensor device for receiving input data from the three-dimensional capacitance sensor device; and a processing system in communication with the data acquisition electronics, the processing system programmed with instructions for executing on the processing system to reconstruct a three-dimensional volume-image from the input data collected by the data acquisition electronics;

wherein the three-dimensional capacitance sensor device is comprised of at least two rows or planes of electrodes to provide sensor sensitivity in the radial and axial directions;

wherein the system is adapted to distribute electric field intensity or sensor sensitivity substantially equally within the three-dimensional capacitance sensor device; and wherein the three-dimensional capacitance sensor device is adapted to provide interrogation of the whole volume of an imaging domain of the three-dimensional capacitance sensor device and wherein the processing system is programmed with instructions for executing on the processing system for reconstructing the three-dimensional volume-image of the vessel interior or other object based on the interrogation of the whole volume of the imaging domain.

* * * * *